United States Patent
Abdel-Monem et al.

(10) Patent No.: US 6,589,794 B2
(45) Date of Patent: Jul. 8, 2003

(54) METHOD FOR THE ANALYSIS OF THE METAL CHELATES OF AMINO ACIDS

(75) Inventors: Mahmoud M. Abdel-Monem, Moscow, ID (US); Michael D. Anderson, Eden Prairie, MN (US)

(73) Assignee: Zinpro Corporation, Eden Prairie, MN (US)

( * ) Notice: Subject to any disclaimer, the term of this patent is extended or adjusted under 35 U.S.C. 154(b) by 316 days.

(21) Appl. No.: 09/810,359

(22) Filed: Mar. 16, 2001

(65) Prior Publication Data

US 2002/0168774 A1 Nov. 14, 2002

(51) Int. Cl.[7] ............................................... G01N 33/20
(52) U.S. Cl. .............................. 436/73; 436/20; 436/76; 436/80; 436/81; 436/83; 436/84
(58) Field of Search ............................... 436/20–22, 73, 436/79–84, 76–77

(56) References Cited

U.S. PATENT DOCUMENTS 4,026,666 A * 5/1977 Holms ........................ 436/20
4,421,858 A * 12/1983 Jackson ...................... 436/20

OTHER PUBLICATIONS

Galdi, M. et al, Journal of Food Science 1988, 53, 1844–1847.*

Pastore, P. et al, Analyst 1999, 124, 837–842.*

Wolf, C. et al, Fresenius J. Anal. Chem. 2000, 368, 839–843.*

Gallaher, D. D. et al, Chemical Abstracts 2001, 134, abstract 192618n.*

Bosscher, D. et al, International Journal of Food Sciences and Nutrition 2001, 52, 173–182.*

* cited by examiner

*Primary Examiner*—Arlen Soderquist
(74) *Attorney, Agent, or Firm*—McKee, Voorhees & Sease, P.L.C

(57) ABSTRACT

A method of assaying metal proteinate samples to determine compliance with European Union standard definitions for such products.

8 Claims, No Drawings

METHOD FOR THE ANALYSIS OF THE METAL CHELATES OF AMINO ACIDS

FIELD OF THE INVENTION

This invention relates to an assay to determine whether metal chelates of amino acids meet the European Union definition necessary for approved sale in member countries.

BACKGROUND OF THE INVENTION

Maintaining the health and well being of domestic animals and poultry requires that essential nutrients be present in the diet in sufficient amounts and in a biologically available form. Because certain nutrients are often deficient in common feed ingredients, supplemental amounts of these nutrients are often added to the feed of domesticated animals and poultry. These feed additives span a wide range of nutrients including vitamins and trace elements. Several feed additives are developed to provide the nutrients in forms that are readily biologically utilizable. The degree of biological availability of nutrients is often referred to as "bioavailability". Bioavailability often depends on the physical and/or chemical properties of the form in which the nutrient is present in the diet. Increased bioavailability of supplemental nutrients (feed additive) is beneficial because it allows the use of lower concentration of the additive in the diet to meet the nutritional needs of animals, while also lowering the potential harmful effects of high levels of incorporation of the additive both on animals and on the environment.

The important role of the trace elements copper, iron, manganese and zinc in animal nutrition has long been recognized. The beneficial effect of iron on blood formation was recognized as early as the 17th century. In 1928, Hart et al. provided the first conclusive evidence that copper was required for recovery from anemia in rats. Zinc was shown to be required for normal growth and health in rats in 1934 and is now considered to be essential for the health of plants, animals and humans. The essential role of manganese for the health of animals and humans has been recognized since 1936.

Many commercial feed additives have been developed to enhance the bioavailability of the trace elements. The beneficial effects of these products are attributed to the association of the metal with an organic molecule, usually called a ligand. This association or bonding results in the increased availability of the metal for utilization by animals, i.e. increased bioavailability. The increased bioavailability of the trace elements in these products is a result of increased solubility, greater stability in the gut, enhanced absorption into circulation and/or improved metabolic utilization.

Most countries regulate the production, labeling, distribution and sale of animal feeds to protect consumers, producers and environment. Different countries have different regulations to govern additives containing trace elements. Most countries require manufacturers to register feed additives containing trace elements before they can be marketed and added to feed. Some countries have strict specifications for feed additives and may require manufacturers to submit detailed analytical methods for the quality assurance of their products. These analytical methods are confidential information and are used by the regulatory agencies only for inspecting the manufacturer's products. Consumers interested in determining the quality of an additive containing trace elements must develop their own methods to examine these products to see if they in fact meet regulatory definitions.

In 1998, the European Union approved the use of a specific group of trace element chelates of amino acids as feed additives. This action is contained as Commission Directive 98/19/EC that amends Directive 70/524/EEC issued on Nov. 23, 1970. The approved additives include copper, iron, manganese and zinc chelates of amino acids hydrate.

The chemical formulas assigned to these additives are:

1) Cupric Chelate of amino acid hydrate, Cu $(X)_{1-3}$. n $H_2O$. X is the anion of any amino acid derived from hydrolyzed Soya Protein. The number of amino acid molecules per metal ion is from 1 to 3. The molecular weight of the hydrated chelate must not exceed 1500.
2) Iron Chelate of amino acid hydrate, Fe $(X)_{1-3}$. n $H_2O$. X is the anion of any amino acid derived from hydrolyzed Soya Protein. The number of amino acid molecules per metal ion is from 1 to 3. The molecular weight of the hydrated chelate must not exceed 1500.
3) Manganese Chelate of amino acid hydrate, Mn $(X)_{1-3}$. n $H_2O$. X is the anion of any amino acid derived from hydrolyzed Soya Protein. The number of amino acid molecules per metal ion is from 1 to 3. The molecular weight of the hydrated chelate must not exceed 1500.
4) Zinc Chelate of amino acid hydrate, Zn $(X)_{1-3}$. $H_2O$. X is the anion of any amino acid derived from hydrolyzed Soya Protein. The number of amino acid molecules per metal ion is from 1 to 3. The molecular weight of the hydrated chelate must not exceed 1500.

The approval of these additives and the above definitions was in response to an application of one manufacturer of these products. However, other manufacturers are allowed to market their products in the European Union countries as long as they assert that their products meet these specifications. In the absence of published methods to assess these products, consumers are unable to make an informed decision regarding their quality and compliance to specifications approved by the EU Commission Directive.

Accordingly, it is a primary objective of this invention to provide a simple method for the analysis of trace metal chelate of amino acids to determine if these products in fact meet the specifications of the EU Commission Directive 70/524/EEC of Nov. 23, 1970 as amended by Commission Directive 98/19/EC.

It is another objective to provide a simple yet reliable test method which can be run using widely available test materials.

It is a yet further objective to provide a test which allows consumers to make their own decisions about whether available products in fact meet the European Union definition.

It is a further objective to provide a test which is also predictive of bioavailability of soluble trace mineral proteinates.

The method and manner of accomplishing these and other objectives of the present invention will be apparent from the detailed description of the invention which follows.

SUMMARY OF THE INVENTION

A simple method for the systematic and comprehensive analysis of trace element chelates of amino acids is described. The metal content of a sample of the trace element chelate of an amino acid is initially determined by using a known appropriate quantitative procedure. An aliquot of the sample is extracted in water or mild acid to simulate the gut and the metal content of the extract is determined to insure the complete extraction of the metal. The extract is then filtered through an ultrafiltration membrane with a nominal molecular weight limit (NMWL) of 500,000 Daltons (500K Daltons) to remove large molecules and insoluble substances including inert carrier. If the product contains carriers/diluents that form gelatinous materials on mixing with water that may clog the ultrafiltration membrane it is removed by centrifugation or vacuum filtration prior to ultrafiltration through the 500,000 Dalton membrane. An aliquot of the 500K ultrafiltrate is filtered through an ultrafiltration membrane with a nominal molecular weight limit of 1500–3000 Daltons. The metal content is determined in an aliquot of the ultrafiltrate. Free and Total amino acids in other aliquots of the ultrafiltrate are determined by using a known and appropriate automated amino acid analyzer. The amino acid profile is then compared to that of soy protein, the only legal source for the EU. Since EU specifications require the product to be made from soy protein, the resulting amino acid profile should be similar to that of soy protein. If wide variations are found, it is indicative that non-soy protein source was used to produce the chelate and it is therefore non-compliant.

Next the concentration of free amino acids in the ultrafiltrate is determined. It must be sufficient to form a 1:1 chelate of the metal but not exceed the concentration sufficient to form 1:3 complex. If not within the limits it is likewise non-compliant with EU standards.

DETAILED DESCRIPTION OF THE PREFERRED EMBODIMENT

In this invention, a method is described for the analysis of metal chelates of amino acids approved for use as feed additives in the European Union countries. This method allows for establishing whether a sample meets the strict specifications of the EU Commission Directive 70/524/EEC of Nov. 23, 1970 as amended by Commission Directive 98/19/EC. A key component of this method is use of ultrafiltration to separate the metal chelates of amino acids with molecular weights <1500 Daltons.

Ultrafiltration is a technique used to segregate substances according to molecular weight and size. The dissolved solution of the trace element proteinate containing molecules of different sizes is passed through a series of semi-permeable membranes. The membranes have pore diameters ranging from 1 to 1,000 Angstroms and under normal operating pressures will separate molecules ranging in molecular weight from 100 to 1,000,000. Each ultrafiltration membrane is characterized by its nominal molecular weight limit (NMWL). NMWL is expressed in kilo Daltons and abbreviated as K or Kd. Molecules with a molecular weight less than the nominal molecular weightless limit of the membrane will pass through the membrane and are found in the ultrafiltrate. Molecules with molecular weight larger than the nominal molecular weight limit of the membrane are retained on the filter. Usually, an ultrafiltration membrane with a stated NMWL will retain at least 90% of a globular solute of that molecular weight in Daltons.

Several known and available technologies are available to separate molecules by ultrafiltration. The most common of these techniques is the pressurized stirred cell system. This system utilizes a closed container in which the ultrafiltration membrane is placed horizontally. The sample is introduced in the cell and the system is pressurized to force water and small molecules through the membrane. The contents of the cell are continuously stirred to prevent the accumulation of retained molecules on the membrane. Another available technology is Centrifuge Separation, which utilizes centrifugal force to push the ultrafiltrate through the membrane. Other available technologies are the tangential flow and Vertical Filtration technologies and these can as well be used to accomplish the desired separation.

The total metal content of the sample is determined by using an appropriate and known quantitative analytical method. An aliquot of the sample is accurately weighed, mixed with water and incubated at from 25° C. to 50° C., preferably 37° C. with occasional shaking for from 30–60 minutes. The mixture is then transferred into a volumetric flask and completed to volume. An accurately measured portion of the extract is filtered through an ultrafiltration membrane with a nominal molecular weight limit (NMWL) of 500,000 Daltons to remove large molecules and insoluble substances including any inert carrier. The metal content of the ultrafiltrate is determined to insure that all the metal was extracted in water. In some products the metal may not be completely extractable in water. In such case the sample can be extracted in acid using the following procedure. An accurately weighed amount of the sample is transferred into a beaker and mixed with sufficient volume of water. The mixture is adjusted to pH 2.0–2.5 by the slow addition of 10% sulfuric acid and incubated at 35° C. for 60 minutes to insure that all the metal chelate is dissolved. The mixture is cooled and adjusted to pH 3.5–4.0 by the careful addition of dilute sodium hydroxide solution. The mixture is then transferred into a volumetric flask and completed to volume. An accurately measured portion of the extract is filtered through an ultrafiltration membrane with a nominal molecular weight limit (NMWL) of 500,000 Daltons to remove large molecules and insoluble substances including any inert carrier. Some products contain carriers/diluents that form gelatinous materials on mixing with water that may clog the ultrafiltration membrane. In this case it is advisable but not required to remove these gelatinous materials by centrifugation or vacuum filtration prior to ultrafiltration through the 500,000 Dalton membrane. The metal content of the ultrafiltrate is determined to insure that all the metal is extracted by using the dilute acid. If all the metal is not extracted in mild acid it is concluded that the metal in the product will not be biologically available after ingestion by the animal.

An accurately measured aliquot of the 500,000 Daltons ultrafiltrate is filtered through an ultrafiltration membrane with nominal molecular weight limit of 3000 Daltons. This will allow molecules of a molecular weight <3000 Daltons to pass through and be collected in the ultrafiltrate. All molecules in the sample that have a molecular weight >3000 will be retained on top of the filter and do not meet EU specifications for Chelate. The specification for metal chelate of amino acid hydrate in the EU is that the chelates have a molecular weight <1500. The use of a membrane with a nominal molecular weight limit of 3000 Dalton insures that all compounds that have a molecular weight of 1500 or less will be present in the filtrate and not retained on the filter. If none pass through the membrane, the sample is non-compliant.

It is desirable or preferred but not required to remove the metal from the ultrafiltrate to eliminate any possibility of interference with the subsequent determination of the amino acids. The metal may be removed by precipitation as the metal phosphate. The sample solution is heated with stirring and a solution of dibasic potassium phosphate is added slowly to allow the metal phosphate to form a crystalline material that can be removed easily by filtration. Other known and appropriate methods for the removal of the metal may also be used.

The total amino acids content of the 3000 Daltons ultrafiltrate is determined by using the AOAC Official Method 994.12 or an equally reliable method. In this step the ultrafiltrate is first hydrolyzed with acid to break down any proteins and peptides to single amino acids. This is followed by the determination of the individual amino acids by using an automated amino acids analyzer. This analysis will determine the total amino acids in the ultrafiltrate, both those that are present as the individual amino acids and those that are produced by hydrolysis of protein and/or peptides. EU chelate specifications require the product to be produced from soy protein. The resulting amino acid profile should be similar to the amino acid profile of soy protein. If wide variations are found, it may be assumed that a non-soy protein source was used to produce the chelate and that the tested sample is non-compliant.

The free amino acids in the 3000 Daltons ultrafiltrate is also determined by using the AOAC Official Method 994.12, or an equally reliable method, excluding the hydrolysis step. In this step the individual amino acids are determined directly by using an automated amino acids analyzer without prior acid hydrolysis. This analysis will determine the amount of individual amino acids originally present in the sample as required by EU Chelate specifications. The content of free amino acids should be similar to that of the total amino acids in the ultrafiltrate within the acceptable experimental errors of the analytical laboratory. If the concentration of total amino acids in the ultrafiltrate is significantly higher than that of the free amino acids, it may be assumed that the ultrafiltrate contains un-hydrolyzed peptides of molecular weight <3000 Daltons. EU chelate specifications require the product to be made from soy protein. The resulting free amino acid profile should be similar to the amino acid profile of soy protein. If wide variations are found, it may be assumed that a non-soy protein source was used to produce the chelate.

The mmoles of each of the amino acids present in the sample are calculated. From the sum of the mmoles of all amino acids and the amount of metal in the sample, the molar ratio of amino acids to metal in the sample is determined and the fraction of metal that is bound to amino acids is calculated.

The following examples are offered to illustrate the applications of this invention in the analysis of some commercial metal chelates of amino acids marketed as feed additives in the European Union countries. Some of these commercial products appear to meet the EU specifications. However, some of the products currently marketed in the EU countries as demonstrated below did not meet these specifications.

EXAMPLE 1

Analysis of a Zinc Chelate of Amino Acids

A sample of commercial product of zinc chelate of amino acids sold in the EU countries containing 10% zinc and claiming to comply with the EU Commission's requirements was analyzed using the method described in this invention.

An aliquot of the sample was accurately weighed. The weight of the sample was 11.3642 g. The aliquot was mixed with water (200 ml) and incubated at 37° C. with occasional shaking for 60 minutes. The mixture was transferred into a 250-ml volumetric flask, cooled and completed to volume with water. A 200 ml aliquot was transferred into a stirred ultrafiltration cell (Amicon 8400) fitted with a polysulfone membrane with a nominal molecular weight limit of 500,000 Daltons (Millipore ZM500, Dia: 76 mm). The sample was filtered under nitrogen at 50 psi. The ultrafiltrate was collected in a 250-ml volumetric flask. The cell and filter were washed four times by placing 10 ml of distilled water in the stirred cell and passing the wash through the membrane under 50 psi of nitrogen. The washings were collected in the same 250-ml volumetric flask as the filtrate. The ultrafiltrate was completed to volume with distilled water. The zinc content of the ultrafiltrate was determined and the result indicated that the sample contained 11.56% zinc. The ultrafiltrate was marked "Ultrafiltrate A" and saved for possible use in the following steps.

A second 11.3563 g aliquot of the sample was accurately weighed and mixed with water (150 ml). The mixture was adjusted to pH 2.2 by the slow addition of 10% sulfuric acid and incubated at 37° C. with occasional shaking for 60 minutes. The mixture was cooled and adjusted to pH 3.5 by the careful addition of dilute sodium hydroxide solution. The mixture was transferred into a 250-ml volumetric flask, cooled and completed to volume with water. A 200 ml aliquot is transferred into a stirred ultrafiltration cell (Amicon 8400) fitted with a polysulfone membrane with a nominal molecular weight limit of 500,000 Daltons (Millipore ZM500, Dia: 76 mm). The sample was filtered under nitrogen at 50 psi. The ultrafiltrate was collected in a 250-ml volumetric flask. The cell and filter were washed four times by placing 10 ml of distilled water in the stirred cell and passing the wash through the membrane under 50 psi of nitrogen. The washings were collected in the same 250-ml volumetric flask as the filtrate. The ultrafiltrate was completed to volume with distilled water and marked "Ultrafiltrate B". The zinc content of "Ultrafiltrate B" was determined and found to be similar to that in "Ultrafiltrate A" indicating that the zinc present in this sample is completely soluble in water. The "Ultrafiltrate B" was discarded.

A 150 ml aliquot of "Ultrafiltrate A" was accurately measured into a stirred ultrafiltration cell (Amicon 8200) fitted with a regenerated cellulose membrane with a nominal molecular weight limit of 3000 Daltons (Millipore YM3, Dia: 63.5 mm). The sample was filtered under nitrogen at 50 psi. The ultrafiltrate was collected in a 250-ml volumetric flask. The cell and filter were washed four times by placing 10 ml of distilled water in the stirred cell and passing the wash through the membrane under 50 psi of nitrogen. The washings were collected in the same 250-ml volumetric flask as the filtrate. The ultrafiltrate was completed to volume with distilled water and mark "3K Ultrafiltrate". The zinc content of the "3K Ultrafiltrate" was determined and indicated that over 98% of the zinc present in "Ultrafiltrate A" was recovered in the "3K Ultrafiltrate".

A 75 ml aliquot of "3K Ultrafiltrate" was accurately measured into a 400-ml beaker and heated to boiling with stirring (using a magnetic stir bar). A 3.0 M dibasic potassium phosphate solution was added slowly until the precipitation of zinc as zinc phosphate was complete. The solution was cooled and filtered. The filtrate was transferred into 100-ml volumetric flask and completed to volume. The solution was submitted to a commercial laboratory for the determination of total and free amino acids by the AOAC Official Method 994.12 using an automated amino acids analyzer. Total amino acids were determined after acid treatment of the sample to hydrolyze small peptides. Free amino acids were determined directly without hydrolysis. The amino acid contents of the original sample were calculated from these results and reported in TABLE 1.

In TABLE 1, the results of amino acids analysis are reported as grams/100 grams of the original sample. In addition to the weight of each amino acid, the mmoles present in 100g are calculated. From the sum of the mmoles of all amino acids and the amount of zinc present in the original sample it is possible to determine the type of complex present and the fraction of zinc bound to amino acids. From the results reported in TABLE 1, it is concluded that this product contains a 1:1 zinc-amino acids complexes and that sufficient amount of free amino acids is present to bind over 91% of the zinc claimed on the label. It is also concluded that the zinc-amino acid complexes have molecular weights less than 1500 Daltons. This product clearly meets the specifications approved by the EU Commission.

TABLE 1

| AMINO ACID | F.W. | % TOTAL | MMOLES, TOTAL | % Free | MMOLES, FREE |
|---|---|---|---|---|---|
| Aspartic Acid | 133.10 | 2.18 | 16.379 | 2.26 | 16.980 |
| Threonine | 119.12 | 0.70 | 5.876 | 0.67 | 5.625 |
| Serine | 105.09 | 1.01 | 9.611 | 1.11 | 10.562 |
| Glutamic Acid | 147.13 | 3.71 | 25.216 | 3.47 | 23.585 |
| Proline | 115.13 | 1.04 | 9.033 | 1.14 | 9.902 |
| Glycine | 75.07 | 0.85 | 11.323 | 0.91 | 12.122 |
| Alanine | 89.09 | 0.82 | 9.204 | 0.85 | 9.541 |
| Valine | 117.15 | 0.99 | 8.451 | 0.80 | 6.829 |
| Methionine | 149.21 | 0.34 | 2.279 | 0.32 | 2.145 |
| Isoleucine | 131.18 | 0.88 | 6.708 | 0.70 | 5.336 |
| Leucine | 131.18 | 1.48 | 11.282 | 1.38 | 10.520 |
| Tyrosine | 181.19 | 0.55 | 3.035 | 0.63 | 3.477 |
| Phenylalanine | 165.19 | 0.93 | 5.630 | 0.97 | 5.872 |
| Histidine | 155.16 | 0.43 | 2.771 | 0.41 | 2.642 |
| Lysine | 146.19 | 1.10 | 7.524 | 1.08 | 7.388 |
| Arginine | 174.20 | 1.47 | 8.439 | 1.34 | 7.692 |
| Total | | 18.48 | 142.762 | 18.04 | 140.217 |
| Zinc Bound | | 9.33 | | 9.17 | |
| % of label claim bound | | 93.34 | | 91.67 | |

EXAMPLE 2

Analysis of a Zinc Chelate of Amino Acids

A sample of another commercial product of zinc chelate of amino acids sold in the EU countries containing 15% zinc and assumed to comply with the EU Commission's requirements was analyzed using the method described in this invention.

A 6.7172 9 aliquot of the sample was accurately weighed and mixed with water (200 ml). The mixture was incubated at 37° C. with occasional shaking for 60 minutes. The mixture was transferred into a 250-ml volumetric flask, cooled and completed to volume with water. A 200 ml aliquot is transferred into a stirred ultrafiltration cell (Amicon 8400) fitted with a polysulfone membrane with a nominal molecular weight limit of 500,000 Daltons (Millipore ZM500, Dia: 76 mm). The sample was filtered under nitrogen at 50 psi. The ultrafiltrate was collected in a 250-ml volumetric flask. The cell and filter were washed four times by placing 10 ml of distilled water in the stirred cell and passing the wash through the membrane under 50 psi of nitrogen. The washings were collected in the same 250-ml volumetric flask as the filtrate. The ultrafiltrate was completed to volume with distilled water. The zinc content of the ultrafiltrate was determined and the sample was found to contain 6.91% zinc. The ultrafiltrate was marked "Ultrafiltrate A" and saved for possible use in the following steps.

A second 6.7590 g aliquot of the sample was accurately weighed and mixed with water (150 ml). The mixture was adjusted to pH 2.2 by the slow addition of 10% sulfuric acid and incubated at 370 C. with occasional shaking for 60 minutes. The mixture was cooled and adjusted to pH 3.5 by the careful addition of dilute sodium hydroxide solution. The mixture was transferred into 250-ml volumetric flask, cooled and completed to volume with water. A 200 ml aliquot is transferred into a stirred ultrafiltration cell (Amicon 8400) fitted with polysulfone membrane with a nominal molecular weight limit of 500,000 Daltons (Millipore ZM500, Dia: 76 mm). The sample was filtered under nitrogen at 50 psi. The ultrafiltrate was collected in a 250-ml volumetric flask. The cell and filter were washed four times by placing 10 ml of distilled water in the stirred cell and passing the wash through the membrane under 50 psi of nitrogen. The washings were collected in the same 250-ml volumetric flask as the filtrate. The ultrafiltrate was completed to volume with distilled water and marked "Ultrafiltrate B". The zinc content of "Ultrafiltrate B" was determined and the sample was found to contain 16.06% zinc. This indicated that the zinc content in this sample was not completely soluble in water but is soluble in dilute acid. The "Ultrafiltrate B" and used for the following steps and "Ultrafiltrate A" was discarded.

A 150 ml aliquot of "Ultrafiltrate B" was accurately measured into a stirred ultrafiltration cell (Amicon 8200) fitted with a regenerated cellulose membrane with a nominal molecular weight limit of 3000 Daltons (Millipore YM3, Dia: 63.5 mm). The sample was filtered under nitrogen at 50 psi. The ultrafiltrate was collected in a 250-ml volumetric flask. The cell and filter were washed four times by placing 10 ml of distilled water in the stirred cell and passing the wash through the membrane under 50 psi of nitrogen. The washings were collected in the same 250-ml volumetric flask as the filtrate. The ultrafiltrate was completed to volume with distilled water and mark "3K Ultrafiltrate". The zinc content of the "3K Ultrafiltrate" was determined and indicated that over 98% of the zinc present in "Ultrafiltrate B" was recovered in the "3K Ultrafiltrate".

A 75 ml aliquot of "3K Ultrafiltrate" was accurately measured into a 400-ml beaker and heated to boiling with stirred (using a magnetic stir bar). A 3.0 M dibasic potassium phosphate solution was added slowly until the precipitation of zinc was complete. The solution was cooled and filtered. The filtrate was transferred into 100-ml volumetric flask and completed to volume. The solution was submitted to a commercial laboratory for the determination of total and free amino acids by the AOAC Official Method 994.12 using an automated amino acids analyzer. Total amino acids were determined after acid treatment of the sample to hydrolyze small peptides. Free amino acids were determined directly without hydrolysis. The amino acid contents of the original sample were calculated from these results and reported in TABLE 2.

In TABLE 2, the results of amino acids analysis are reported as grams/100 grams of the original sample. In addition to the weight of each amino acid, the mmoles present in 100 g are calculated. From the sum of the mmoles of all amino acids and the amount of zinc in the original sample, it is possible to determine the type of complex present and the fraction of the zinc that is bound to amino acids. From the results reported in TABLE 2, it is concluded that the amount of free amino acids present in this product is sufficient to bind only 7.75% of the zinc claimed on the label if the complexes are 1:1 zinc-amino acids complexes. These results clearly indicate that this product does not meet the specifications of the EU Commission's directive.

TABLE 2

| AMINO ACID | F.W. | % TOTAL | MMOLES, TOTAL | % Free | MMOLES, FREE |
|---|---|---|---|---|---|
| Aspartic Acid | 133.10 | 0.14 | 1.052 | 0.08 | 0.601 |
| Threonine | 119.12 | 0.04 | 0.336 | 0.01 | 0.084 |
| Serine | 105.09 | 0.06 | 0.0571 | 0.01 | 0.095 |
| Glutamic Acid | 147.13 | 1.80 | 12.234 | 1.91 | 12.982 |
| Proline | 115.13 | 0.12 | 1.042 | 0.03 | 0.261 |
| Glycine | 75.07 | 0.15 | 1.998 | 0.10 | 1.332 |
| Alanine | 89.09 | 0.09 | 1.010 | 0.03 | 0.337 |
| Valine | 117.15 | 0.05 | 0.427 | 0.02 | 0.171 |
| Methionine | 149.21 | 0.02 | 0.134 | 0.01 | 0.034 |
| Isoleucine | 131.18 | 0.04 | 0.305 | 0.01 | 0.076 |
| Leucine | 131.18 | 0.10 | 0.762 | 0.03 | 0.229 |
| Tyrosine | 181.19 | 0.04 | 0.221 | 0.01 | 0.055 |
| Phenylalanine | 165.19 | 0.05 | 0.303 | 0.03 | 0.182 |
| Histidine | 155.16 | 0.03 | 0.193 | 0.01 | 0.064 |
| Lysine | 146.19 | 0.17 | 1.163 | 0.17 | 1.163 |
| Arginine | 174.20 | 0.05 | 0.287 | 0.02 | 0.115 |
| Total | | 2.95 | 22.038 | 2.48 | 17.779 |
| Zinc Bound | | 1.44 | | 1.16 | |
| % of label claim bound | | 9.61 | | 7.75 | |

From the above examples, it can be seen how the series of steps of the method or assay here described can provide a data profile as illustrated in Table 1 and Table 2 which tells whether a product meets the legal criteria necessary for approved sale in the EU. The invention therefore accomplishes its stated objectives.

Finally, it goes without saying, that some modifications to the test steps and procedures outlined here and a successful assay can still be achieved. Such modifications are envisioned to come within the scope of the invention.

What is claimed is:

1. A method of determining metal amino acid chelates in protein products comprising:
   preparing a sample of dissolved metal proteinate;
   ultrafiltering the sample of the dissolved metal proteinate through a first molecular weight membrane having a cutoff of between 100,000 and 500,000 Daltons to provide a first ultrafiltrate;
   ultrafiltering the first ultrafiltrate through a second molecular weight membrane have a cutoff of between 1,500 and 3,000 Daltons to provide a second ultrafiltrate;
   thereafter determining the metal and free amino acid content of the second ultrafiltrate.

2. The method of claim 1 wherein the dissolved metal proteinate is dissolved in water.

3. The method of claim 1 wherein the metal proteinate is dissolved in a 2.0 to 2.5 pH acid solution.

4. The method of claim 1 wherein the first molecular weight membrane is a 500,000 Dalton membrane.

5. The method of claim 1 wherein the second molecular weight membrane is a 3,000 Dalton membrane.

6. The method of claim 1 further comprising
   comparing the amino acid content of the second ultrafiltrate to that of standard soy protein concentrate and
   assessing whether the metal proteinate is a soy product.

7. The method of claim 1 wherein metal is removed from the second ultrafiltrate before determining the amino acid content.

8. The method of claim 7 wherein metal is removed by precipitation as metal phosphate.

* * * * *